US00PP30243P2

(12) United States Plant Patent
Horvath

(10) Patent No.: US PP30,243 P2
(45) Date of Patent: Feb. 26, 2019

(54) ***STACHYS* PLANT NAMED 'SUMMER ROMANCE'**

(50) Latin Name: *Stachys*
Varietal Denomination: Summer Romance

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 10 days.

(21) Appl. No.: 15/530,282

(22) Filed: Dec. 20, 2016

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new, distinct *Stachys* plant as shown and described, characterized by the longer pink purple flower clusters with more flowers as compared to the seed parent.

1 Drawing Sheet

Latin name: *Stachys.*
Cultivar name: 'Summer Romance'.

BACKGROUND OF THE INVENTION

The present invention relates to a new and distinct hybrid of *Stachys* plant named 'Summer Romance' characterized by the longer pink purple flower clusters with more flowers as compared to the seed parent. The new *Stachys* was raised as a seedling from open pollinated seed sown from the seed parent *Stachys* 'Hummelo', not patented, in Hebron, Ill. in 2009. The selection of the new plant was due to its' longer and more pink purple flower clusters with more flowers, compared to the seed parent. Initial asexual reproduction has taken place at a nursery in Hebron, Ill. since 2010 by means of division, and vegetative cuttings. The new *Stachys* has shown to be stable and identical in reproduction to the parent after rooting over 1400 plants from 2010 to 2016. No plants of the new *Stachys* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Stachys* plant named 'Summer Romance' characterized by the longer pink purple flower clusters with more flowers as compared to the seed parent have been observed to be unique and stable. For purpose of comparison the new plant will be referred to as 'Summer Romance'.

Plants of 'Summer Romance' can be compared to the seed parent plant of *Stachys* 'Hummelo', not patented. 1. The 'Summer Romance' plant is taller, growing to 75 cm while *Stachys* 'Hummelo' grows to 40 cm. 2. The 'Summer Romance' plant has a flower color of N78 B while *Stachys* 'Hummelo' has a flower color of 77 A.

Plants of 'Summer Romance' can also be compared to a pink flowered *Stachys*, 'Pink Cotton Candy', U.S. Pat. No. 21,436, patented. 1. The 'Summer Romance' plant is taller growing to 75 cm while *Stachys* 'Pink Cotton Candy' grows to 47 to 50 cm. 2. The 'Summer Romance' plant has a flower color of N78 B while *Stachys* 'Pink Cotton Candy' has a flower bi-color of N66 A and between 61 A and B.

DESCRIPTION OF PHOTOGRAPHS

Figure 1:
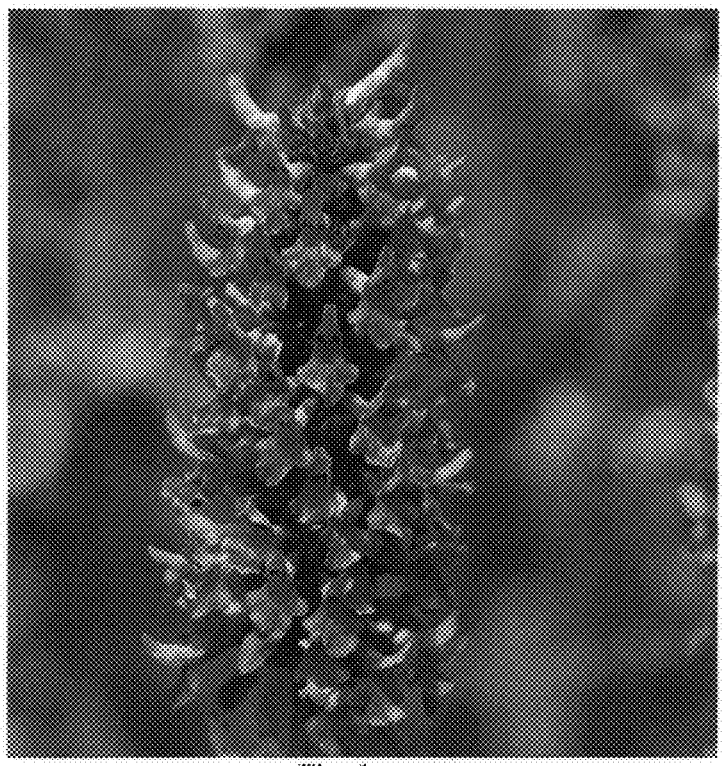
Figure 2:
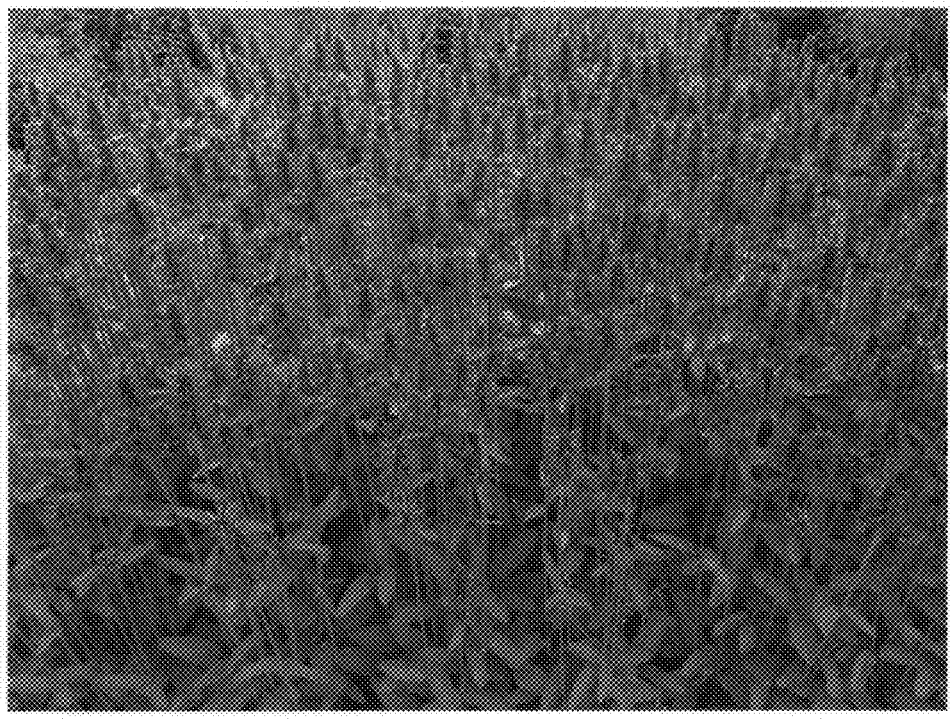

Plants pictured in the drawing were grown for two years.
FIG. 1. Close up of the flower.
FIG. 2. A group of potted plants.

DETAILED BOTANICAL DESCRIPTION

In the following description, color references are made to The Royal Horticultural Society Colour Chart (2001). Plants used for the description were grown for two years in a 1 gallon pot. Measurements and numerical values represent averages of typical plants.

PLANT

Botanical classification: *Stachys* hybrid.
Form: Globular shape.
Height: 75 cm from soil to top of flowers; 50 cm wide.
Growth: Herbaceous perennial, broad upright, moderate vigor.
*Roots.*—Fine, compact, dense, freely branching, white.
Stem:
*Form.*—Quadrangular, strong.
*Color.*—145 A.
*Pubescence.*—Densely covered with short green white hairs, about 1-2 mm long.
Branching: No.
*Form.*—Basal stems, no pinching required.
*Diameter.*—5 mm.
*Length.*—75 cm.
*Internode length.*—Range from 7 cm to 24 cm long.
*Quantity.*—About 20 flowering lateral stems.
Foliage:
*Arrangement.*—Opposite.
*Number of leaves per stem.*—4, 2 pairs.
*Size of leaf.*—Length: 10 cm, shorter at tops of stems. Width: 43 mm.

*Shape of leaf*.—Oval.
*Shape of tip*.—Obtuse.
*Shape of base*.—Sagittate.
*Texture*.—Rugose.
*Pubescence*.—Very dense rugose hairs, light green-white, less than 1-2 mm long on underside of main vein.
*Margin type*.—Dentate.
*Color*.—Young and Mature leaves: Upper surface: Close to 137 C. Lower surface: Close to 146 C.
*Petioles*.—Length: 20 mm. Diameter: 2-3 mm, 8 mm at base. Color: Top: 145 A, Bottom 145 C.
*Veins*.—Pattern: Pinnate. Color: Upper surface: close to 137 C. Lower surface: 145 C.

Durability: Highly durable to stresses; when crushed, foliage spreads typical odor.

Response time to flower: About 10 months when grown in the containers.

FLOWER

Natural flowering season: Continuous from June into July.

Inflorescence type and habit: Terminal verticillaster, labiate, no fragrance, flower lasts about three weeks on plant, self-cleaning.

Rate of flower opening: About 50-75% of flowers open at once, all flowers open in about 4 weeks.

Number of flowers: About 90 per spike; 20 stems, 1800 flowers per plant.

Inflorescence size:
*Diameter*.—5 cm.
*Height*.—75 cm.

Peduncle:
*Length*.—Up to 20 cm.
*Diameter*.—2 mm.
*Color*.—Top lip N78 B with some dark areas N78 A, Bottom N78 C.
*Orientation*.—Upright.
*Strength*.—Strong.

Corolla:
*Petal arrangement*.—Labiate with one upper lip and one 3-lobed lower lips having one main lobe and two smaller side lobes.
*Overall size*.—10 mm high; 6 mm wide.
*Margin*.—Entire upper lip; 3-lobed lower lip.
*Tip shape*.—Emarginate upper lip; rounded lower lip.
*Length*.—Average upper lip: 7 mm; average lower lip: 5 mm.
*Width*.—Average upper lip: 4 mm; average lower lip: 6 mm.
*Petal quantity*.—2, fused at base.
*Petal apex shape*.—Upper lip; broad elliptic; folded; lower lip spathulate.
*Texture*.—Glabrous.
*Aspect*.—Drooping.
*Petaloids*.—None.

Color:
*Petals*.—When opening: Upper surface: N78 B. Lower surface: N78 C. Fully opened: N78 B. Lower surface: N78 C.

Bud:
*Shape*.—Obovate.
*Length*.—10 mm.
*Diameter*.—3 mm width.
*Color*.—N78 B.

Calyx:
*Arrangement*.—5 sepals fused into a tube at 90% of the length; 3 upper sepals fused nearly at the tips; 2 lower sepals fused nearly at the tips.
*Height*.—7 mm length.
*Diameter*.—3 mm.
*Shape*.—Tubular.
*Sepals*.—Shape: Elliptic with acute tip and crenate base. Size: Average 7 mm long; 1 mm wide. Margin: Entire. Texture: Grayish hairs; less than 0.2 mm long. Color: Outer surface: N77 C at the top third and green 145 C at the base. Inner surface: from the tips down N77 C to green 145 C at the base. Bracts: 2 bracts under each whorl of flowers; deltoid shape with apiculate tip; upper surface 145 C lower surface 145 C with N77 C spot or streaks.
*Odor*.—Present in petals and sepals.

REPRODUCTIVE ORGANS

Stamens:
*Number*.—4.
*Filament length*.—3-4 mm.
*Anthers*.—Shape: Basifixed, elliptic. Length: 0.5 mm. Color: Dark with white pollen, too small to measure color.
*Pollen*.—Color: white; too little to determine color. Amount: very low.

Pistil:
*Number*.—One.
*Length*.—11 mm.
*Style*.—Length: 11 mm. Color: N155 B at the top half fading to white at the base.
*Stigma*.—Shape: Cleft (2 parted). Color: N155 B. Ovary color: 145 B.

Seeds and fruits: Yes, brown and round 0.5 mm long and 0.5 mm wide, color 200 B.

Disease/pest resistance: No unusual susceptibility to diseases or pests has been noted to date.

Temperature tolerance: Tolerate to heat at least up to 30° C. and cool at least down to USDA Zone 5.

I claim:

1. A new, distinct *Stachys* plant as shown and described, characterized by the longer pink purple flower clusters with more flowers when compared to the seed parent.

* * * * *